(12) United States Patent
Koehler et al.

(10) Patent No.: US 6,442,229 B1
(45) Date of Patent: Aug. 27, 2002

(54) COMPUTED TOMOGRAPHY APPARATUS INVOLVING A CONICAL RADIATION BEAM AND A HELICAL RELATIVE MOTION

(75) Inventors: Thomas Koehler, Norderstedt; Michael Grass, Hamburg, both of (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/969,009

(22) Filed: Oct. 2, 2001

(30) Foreign Application Priority Data

Oct. 5, 2000 (DE) .......................................... 100-49-380

(51) Int. Cl.$^7$ ................................................ G01N 23/00
(52) U.S. Cl. ............................................. 378/15; 378/4
(58) Field of Search ...................................... 378/4–20

Primary Examiner—Craig E. Church
(74) Attorney, Agent, or Firm—John Vodopia

(57) ABSTRACT

The invention relates to a computed tomography apparatus wherein the start position and/or the stop position for a helical relative motion between the radiation source, generating a conical radiation beam, on the one side and the examination zone on the other side are adjusted in such a manner that the zones that, at the beginning and/or the end, are irradiated by the radiation beam to an extent which does not suffice for reconstruction become larger underneath the table top, in the direction of the axis of rotation, than above the table top.

5 Claims, 4 Drawing Sheets

Figure 1:
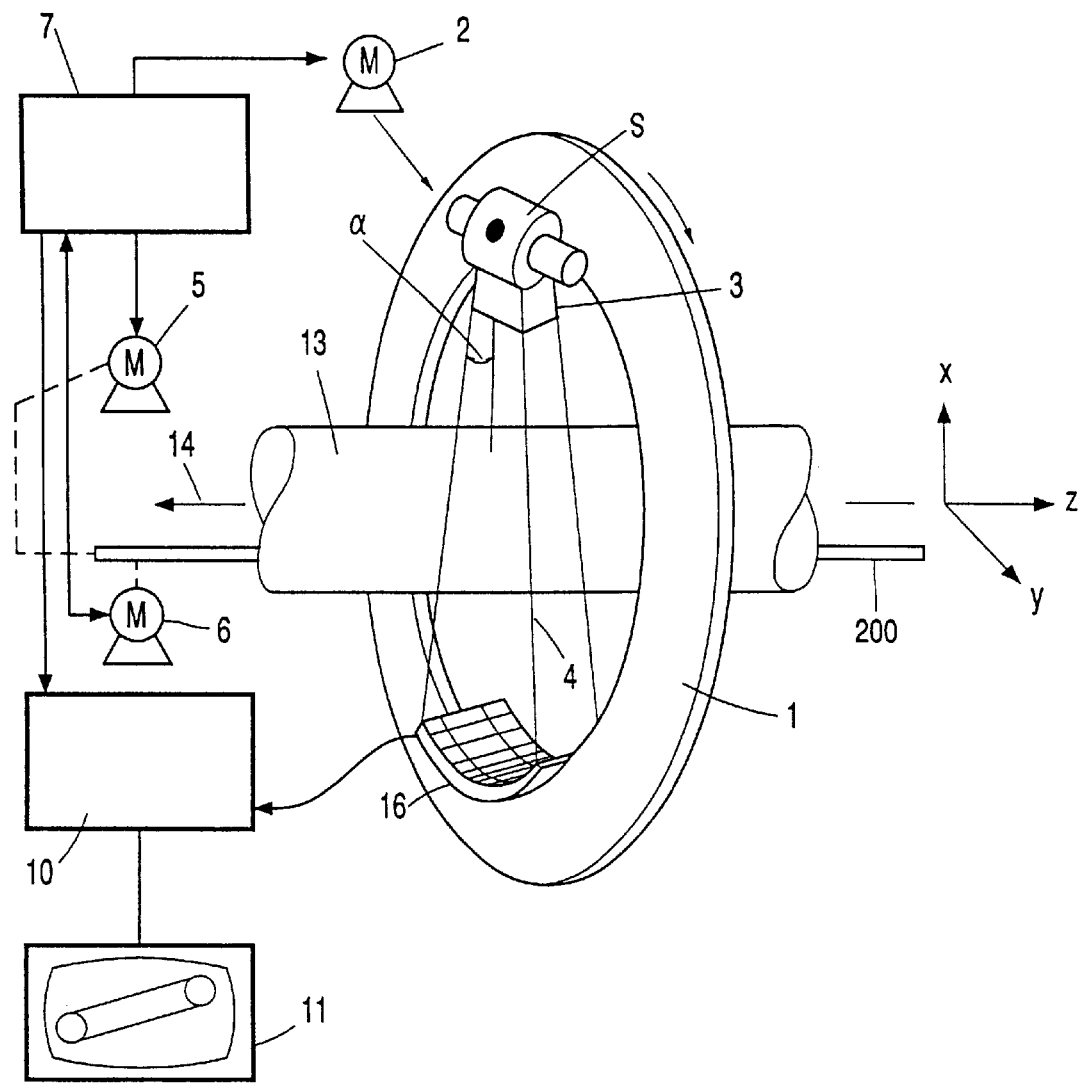

COMPUTED TOMOGRAPHY APPARATUS INVOLVING A CONICAL RADIATION BEAM AND A HELICAL RELATIVE MOTION

The invention relates to a computed tomography apparatus which includes a radiation source which emits a conical radiation beam and moves along a helical path relative to an examination zone or an object present therein. In computed tomography apparatus of this kind (for example, as known from U.S. application Ser. No. 09/380972 (PHQ 98-020)), the absorption cannot be reconstructed without artefacts in the zones that are scanned by the conical radiation beam at the beginning or the end of a CT examination, because the radiation source irradiates these zones from a limited angular range only.

The ratio of the zone that is exposed to radiation to the zone that can be reconstructed without artefacts is less favorable as the angle of aperture of the radiation beam (in two mutually perpendicular planes) is larger. Thus, only a part of the radiation can be used for the CT imaging; in the case of medical examinations this leads to an unnecessarily high radiation load for the patient. When, moreover, the cylindrical examination zone is allowed to begin and end by way of the first and the last layer, respectively, that can be fully reconstructed and extends perpendicularly to the cylindrical examination zone, the circumstances become entirely unfavorable.

Therefore, it is an object of the present invention to improve these conditions. This object is achieved in accordance with the invention by means of a computed tomography apparatus which includes:

- a scanning unit which includes a radiation source and a detector unit which is connected thereto in order to detect a conical radiation beam, emitted by the radiation source, after its passage through an examination zone (13), or an object arranged on a table top situated therein, and to generate corresponding CT data,
- a drive device (2, 5) for producing a relative motion in the form of a helix, including a rotation about an axis of rotation (14) and a displacement parallel to the axis of rotation, between the scanning unit (S, 16) and the examination zone (13) or the object,
- a reconstruction unit for reconstructing a three-dimensional CT image from the measuring values produced by the detector unit, and
- a control unit for controlling the radiation source and the drive device in such a manner that emission of the radiation beam by the radiation source commences in a start position such and/or ends in a stop position such that the zones which, at the beginning and/or the end of the emission, are irradiated by the radiation beam only to an extent that is not adequate for reconstruction, are larger underneath the table top, in the direction of the axis of rotation, than above the table top.

The invention is based on the recognition of the fact that the cylindrical part of the examination zone for which complete reconstruction is possible is bounded on both sides by end faces which do not extend perpendicularly to the axis of rotation and are not flat either. When the start position and/or the stop position are suitably chosen, it can be achieved that (measured in the direction of the axis of rotation) the part of the examination zone that can be reconstructed is larger above the table than below the table (or that the part that cannot be reconstructed is larger underneath the table than above the table).

The zone that can be imaged by way of layers extending perpendicularly to the axis of rotation can then be selected in conformity with the dimensions of the zone that can be reconstructed above the table. Granted, in that case the zone situated underneath the table can no longer be reconstructed in the layers situated at the edge; however, this limitation is irrelevant, because the object, and hence the region of interest for the diagnosis, are situated above the table.

The optimum start and stop positions of the radiation source are usually situated above a horizontal plane that contains the axis of rotation. The exact start and stop positions, however, are also dependent on how the measuring values are acquired and on how a three-dimensional CT image is reconstructed from these measuring values. For example, for the CT method disclosed in the previously mentioned publication the optimum start position is obtained in conformity with claim 2 and the stop position in conformity with claim 3.

Because in the case of the known methods the end faces of the zone that can be completely reconstructed are not flat, the optimum start position is also dependent on the level at which the table punctures said end faces. When the table is situated, for example, below the axis of rotation during a CT examination, the start position and the stop position must be shifted by the same angular amount in the direction of revolution. claim 4 describes a version which is suitable for automatically adapting the start position and the stop position to the vertical position of the table.

As has already been stated, the zones that are situated underneath the table top can no longer be completely reconstructed in the layers situated at the ends, so that artefacts occur in these zones. These artefacts can be avoided in conformity with claim 5 where the user is given the normal image impression. The zones that cannot be fully reconstructed underneath the table, however, could also be suitably marked (for example, colored) during display so that the user is not falsely given the impression of a complete reconstruction in this zone.

Figure 2:
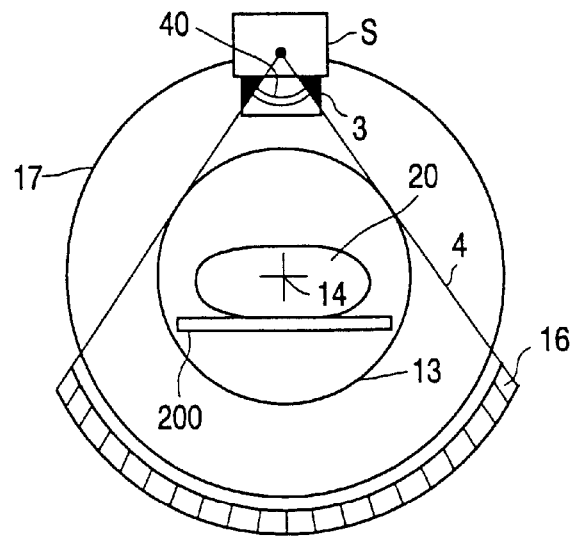
Figure 3:
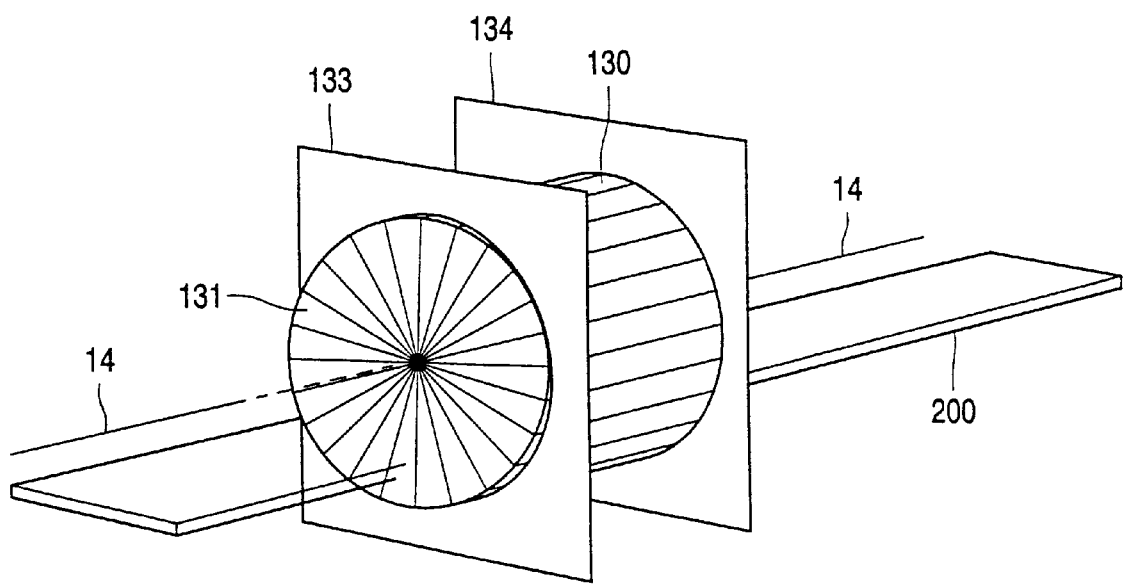
Figures 4A, 4B:
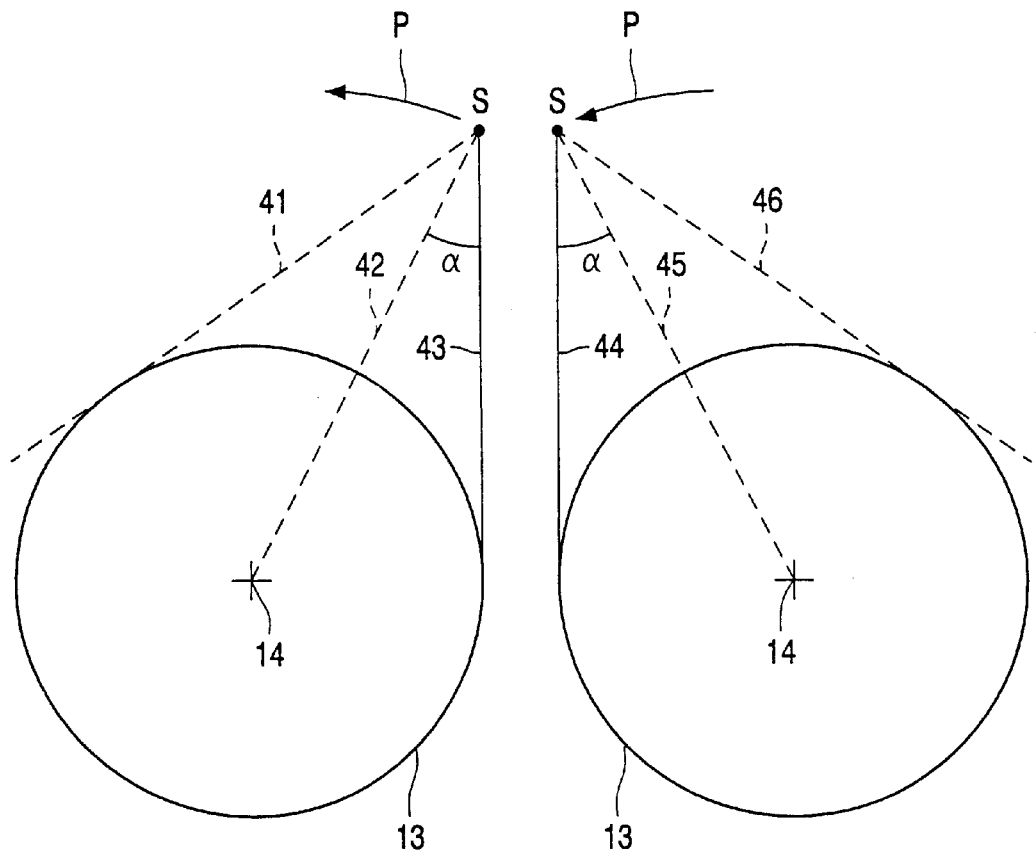
Figures 6A, 6B:
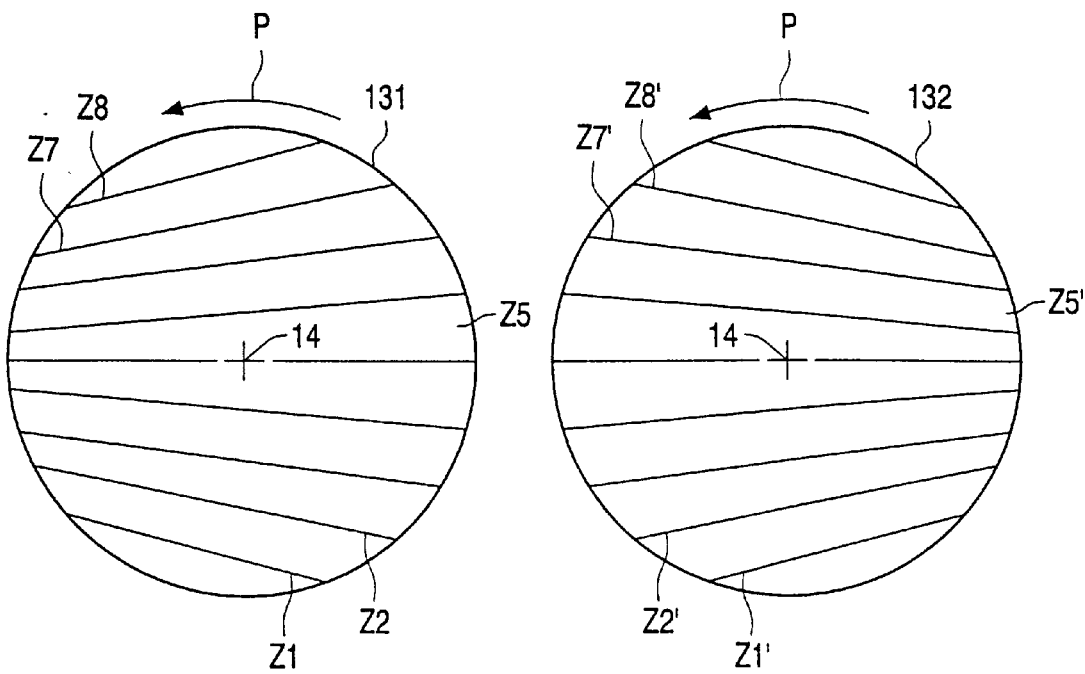
Figure 5:
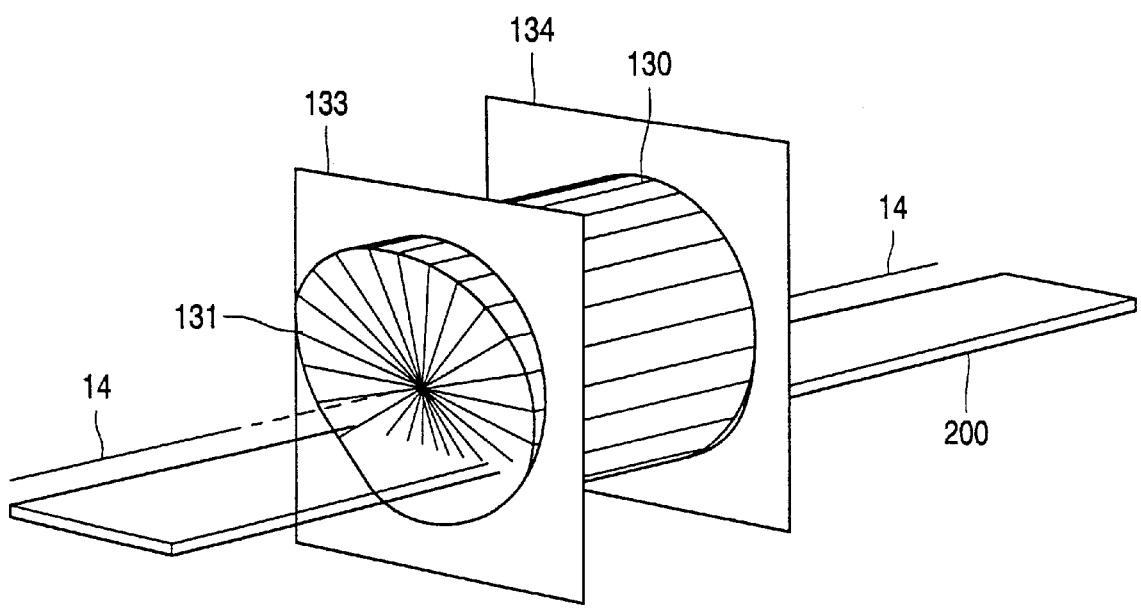

The invention will be described in detail hereinafter with reference to the drawings. Therein:

FIG. 1 is a diagrammatic perspective view of a computed tomography apparatus in accordance with the invention, FIG. 2 is a cross-sectional view of such a computed tomography apparatus, FIG. 3 shows the part of the examination zone that can be reconstructed without using the invention, FIGS. 4a and 4b show the start position and the stop position, respectively, of the radiation source, FIG. 5 shows the part of the examination zone that can be reconstructed in accordance with the invention, and FIG. 6a and FIG. 6b show the end faces of the zone that can be reconstructed.

The computed tomography apparatus shown in the FIGS. 1 and 2 includes a gantry 1 which is capable of rotation about an axis of rotation 14 which extends parallel to the z direction of the system of co-ordinates shown in FIG. 1 (and perpendicular to the plane of drawing of FIG. 2). To this end, the gantry is driven at a preferably constant, but adjustable speed by a motor 2. On the gantry there is mounted a radiation source S, for example an X-ray source. This source is connected to a collimator arrangement 3 which, utilizing inter alia a diaphragm arrangement 40, forms a conical radiation beam from the radiation produced by the radiation source S, that is, a radiation beam having a finite dimension other than zero in the direction of the z axis as well as in a direction perpendicular thereto (that is, in a plane perpendicular to the axis of rotation 14).

The radiation beam irradiates an examination zone 13 in which an object 20, for example a patient arranged on a table top 200 of a patient table (not shown), may be situated. The examination zone 13 is shaped as a cylinder whose diameter is determined by the angle of aperture a of the radiation beam 4 (the angle of aperture is to be understood to mean the angle enclosed by a ray of the radiation beam 4 which is situated at the edge in a plane perpendicular to the axis of rotation 14 relative to the plane defined by the radiation source S and the axis of rotation).

After having traversed the examination zone 13, the X-ray beam 4 is incident on a two-dimensional detector unit 16 which is attached to the gantry 1 and comprises a plurality of detector rows, each of which comprises a plurality of detector elements. The detector rows are arranged in planes which are perpendicular to the axis of rotation 14, that is, preferably on an arc of a circle around the radiation source S. However, they may also be formed in a different way; for example, they may describe an arc of a circle around the axis of rotation 14 or be rectilinear. Each detector element that is struck by the radiation beam 4 supplies a measuring value for a ray of the radiation beam 4 in each position of the radiation source. Such measuring values will also be referred to as CT data hereinafter.

The examination zone 13, or the table top 200, can be displaced parallel to the axis of rotation 14, or parallel to the z axis, by means of a motor 5. Instead, however, the gantry could also be shifted in the opposite direction. This is because only the relative motion between the gantry 1 and the examination zone 13 is of importance during the rotation of the radiation source around the axis of rotation 14 as well as during the displacement of the examination zone in the direction of the axis of rotation 14. When the two motors 5 and 2 run simultaneously, the radiation source S and the detector unit 6 describe a trajectory in the form of a helix relative to the examination zone 13. However, when the motor 5 for the displacement in the z direction is stationary and the motor 2 rotates the gantry 1, a circular trajectory is obtained for the X-ray source S and the detector unit 16 relative to the examination zone 13.

Finally, the height of the table top 200 can be adjusted by means of a motor 6, the instantaneous height of the table being measured at the same time so as to be applied to a control unit 7. The control unit 7 also controls the motors 2, 5 and 6, the radiation source S and the transfer of the CT data from the detector unit 16 to an image processing computer 10. The image processing computer 10 reconstructs a CT image from the CT data; this CT image represents the absorption in the (three-dimensional) part of the examination zone for which an adequate amount of CT data can be acquired.

This part of the examination zone is denoted by the reference numeral 130 in FIG. 3. Its cross-section in a plane perpendicular to the axis of rotation 14 corresponds to the cross-section of the examination zone 13. The zone 130 that can be reconstructed is bounded on both sides by end faces 131 and 132 (the rear end face 132 is not visible in FIG. 3). The end faces, however, do not extend perpendicularly to the axis of rotation and are not flat either. Consequently, only the part of the zone 130 which can be completely reconstructed in layers perpendicular to the axis of rotation will be reproduced (and reconstructed). This part is bounded on both sides by planes 133 and 134 that are perpendicular to the axis of rotation 14. It appears that, for example, the part that is situated between the plane 133 and the end face 131 is lost; in this part the layers would reproduce only a part of the cross-section of the examination zone 13.

In accordance with the invention the start position and the stop position of the radiation source, in which the relative motion between the radiation source and the examination zone and the emission of the radiation beam begins and ends, are chosen in such a manner that the zones of the examination zone that cannot be reconstructed are situated within or below the table top 200. The zones in the layer above the table top which are of interest to the diagnosis and in which the object is situated, however, can be completely reconstructed.

This will be described in detail with reference to the FIGS. 4a and 4b which show the radiation source S in the start position (FIG. 4a) and in the stop position (FIG. 4b), the plane of drawing extending perpendicularly to the axis of rotation 14. In this start position a plane that is defined by the axis of rotation 14 and the radiation source S encloses an angle α (against the direction of rotation denoted by an arrow P) relative to the vertical, which angle corresponds to half the angle of aperture of the radiation beam. It is assumed that use is made of the reconstruction method that is known from the cited document, which method involves rebinning while dealing with radiation beams that are parallel to one another and parallel to the axis of rotation.

In conformity therewith the radiation beam emitted by the radiation source S in the start position can be assumed to be decomposed into a number of fan beams that are parallel to the axis of rotation, the fan beams 41, 42, 43 thereof being shown in FIG. 4a. The fan beams 41 and 42, denoted by dashed lines, are not used for the reconstruction. Only the ray of the fan beam 43 (extending in a vertical plane) that is situated furthest in front in the direction of the relative motion is used.

In the course of further relative motion of the radiation source not only at least one ray from a fan beam in a vertical plane (which, however, is offset to the left relative to the plane of the fan beam 43) is used for the reconstruction, but also rays in fan beams that are not situated in a vertical plane. After one revolution of the radiation source through the angle 2α about the axis of rotation 14, a set of fan beams that are situated in vertical planes has already been emitted this set traverses the examination zone 13 across its entire width. (Fan beams are also emitted in other planes; however, the fan beams that are situated in vertical planes are the first ones to traverse the examination zone across its entire width.)

At their front edge (viewed in the direction of displacement) the vertical fan beams comprise rays which emanate from the respective radiation source position on a segment of the helix and are incident on a segment of the helix present on the other side of the examination zone. These rays define the end face 131 which bounds the volume that can be reconstructed at one side. The angle enclosed by such rays relative to the vertical is dependent on the location; however, the end points of the rays have been offset in the direction of the relative motion with respect to the starting points. Consequently, the shape of the end face 131 as shown in FIG. 5 is obtained, so that in this case the upper part of the zone 130 projects beyond the lower part.

FIG. 4b illustrates the conditions in the stop position in which the plane defined by the radiation source S and the axis of rotation encloses an angle α relative to the vertical in the direction of rotation. Only one of the rays produced in this position is required again, said ray being situated in the fan beam 44 lying in a vertical plane. The rays from the other fan beams 45 and 46, or the associated CT data, are no longer required for the reconstruction. Thus, the end face 132 which terminates the zone 130 on the other side is also formed by rays that extend in vertical planes. The end face at the top again projects further outwards than at the bottom.

When complete reconstruction of the part of the examination zone that is situated in or below the table top 200 is abandoned, the two boundary planes 133 and 134 can be shifted further outwards as appears from a comparison of the FIGS. 3 and 5. However, even when the use is not limited to perpendicular layers, more favorable circumstances are obtained in FIG. 5, because the part of the examination zone that can be reconstructed is larger above the table top 200 than below the table top.

In order to give the user the normal impression also for these parts that cannot be reconstructed, the absorption distribution in layers that are situated further inwards in the zone 130 could be used as a basis. However, it would also be possible to mark the zones that cannot be reconstructed in or below the table top in the image by means of a color.

Because the end faces are not flat, the start positions illustrated with reference to the FIGS. 4a and 4b are optimum only for a very specific height of the table top 200, that is, when the upper surface of the table top 200 is coincident with the axis of rotation 14. When the table top is adjusted so as to be higher or lower, the optimum position is obtained only approximately.

The FIGS. 6a and 6b are a plan view of the end faces 131 and 132 (the direction of viewing being the same in both cases) at the beginning and the end of the volume that can be reconstructed. The arrow P represents the direction of rotation of the radiation source. On the end face 131 there are plotted lines Z1, Z2, . . . Z5 . . . Z7 and Z8 which interconnect the points on the end faces that have the same z coordinate. The line Z5 is punctured by the axis of rotation 14. It is exactly straight and horizontal. The lines therebelow, for example the lines Z1 and Z2, drop off to the right whereas the lines situated thereabove, for example, Z7 and Z8, rise to the right. These lines are only approximately rectilinear.

Optimum conditions are obtained when the upper side of the table top coincides with one of these lines. Therefore, when the table top is situated below the axis of rotation, either the table top should be tilted slightly (which is impossible) or the end face should be rotated slightly in the direction of the arrow P, that is, starting from the position shown in FIG. 6a. This would mean that the end face 131 would no longer be defined by rays from vertical fan beams, but by rays from mutually parallel fan beams which enclose a small angle relative to the vertical so that, for example, the contour line Z2 extends horizontally. This in its turn would imply that the start position is not situated as shown in FIG. 4a, but at an angle in relation to the vertical which is smaller than $\alpha$.

FIG. 6b shows corresponding lines Z1', Z2', . . ., Z5', . . . Z7' and Z8'. It appears that these lines are mirror imaged relative to the lines Z1 . . . Z8 on the end face 131, that is, the lines situated below the axis of rotation rise to the right and the lines situated above the axis of rotation drop off to the right. Consequently, the end face 132 should be rotated against the direction of the arrow P when the table top is situated underneath the axis of rotation. This implies that the stop position is slightly shifted in the direction opposing the direction of rotation, that is, to the same extent as that to which the start position must be shifted in the direction of rotation. Consequently, the stop position is not situated as shown in FIG. 4b, but at an angle of less than $\alpha$ relative to the vertical.

In order to achieve automatic adaptation of the start position and/or the stop position to the instantaneous height of the table top 200, the amount of displacement of the top 200 by the motor 6 (see FIG. 1) is applied to the control unit 7 which determines the optimum start and stop positions in dependence on the relevant height.

The table top 200 is shifted in the z direction proportion to the value of the angle $\alpha$. When the user preselects the shift in the z direction, however, the radiation source that has started from the optimum start position usually cannot finish in the optimum stop position, but in another position. In that case the desired position in space is obtained only for the starting face 131 and not for the end face 132 (in case the start position is chosen so that at the end the optimum stop position is obtained exactly for the desired displacement in the z direction). The optimum position of the reconstruction zone 30 is then situated only at the beginning or at the end of the revolution. In order to avoid this, the displacement in the z direction can also be chosen to be such that only the number n of revolutions is preselected.

What is claimed is:

1. A computed tomography apparatus which includes:

a scanning unit which includes a radiation source (S) and a detector unit (16) which is connected thereto in order to detect a conical radiation beam, emitted by the radiation source, after its passage through an examination zone (13), or an object arranged on a table top therein, and to generate corresponding CT data, a drive device (2, 5) for producing a relative motion in the form of a helix, including a rotation about an axis of rotation (14) and a displacement parallel to the axis of rotation, between the scanning unit (S, 16) and the examination zone (13) or the object, a reconstruction unit for reconstructing a three-dimensional CT image from the measuring values produced by the detector unit, and a control unit for controlling the radiation source and the drive device in such a manner that the emission of the radiation beam by the radiation source commences in a start position such and/or ends in a stop position such that the zones which, at the beginning and/or end of the emission, are irradiated by the radiation beam only to an extent that is not adequate for reconstruction are larger underneath the table top, in the direction of the axis of rotation, than above the table top.

2. A computed tomography apparatus as claimed in claim 1, wherein the radiation source in the start position defines a plane with the axis of rotation which encloses an angle a in the direction opposing the direction of rotation of the radiation source, relative to a perpendicular plane through the axis of rotation, which angle $\alpha$ corresponds to half the angle of aperture of the radiation beam in a plane that is perpendicular to the axis of rotation or is smaller than half the angle of aperture.

3. A computed tomography apparatus as claimed in claim 1, wherein the radiation source in the stop position defines a plane with the axis of rotation which encloses an angle $\alpha$ in the direction of rotation of the radiation source relative to a perpendicular plane through the axis of rotation, which angle a corresponds to half the angle of aperture of the radiation beam in a plane that is perpendicular to the axis of rotation or is larger than half the angle of aperture.

4. A computed tomography apparatus as claimed in claim 1, including means for measuring the vertical position of the table top and means for changing the start position and/or the stop position in dependence on the vertical position of the table top.

5. A computed tomography apparatus as claimed in claim 1, wherein the reconstruction unit is programmed in such a manner that for the zones in or underneath the table top which, at the beginning and/or at the end of the emission, are irradiated by the radiation beam to an extent that is not adequate for the reconstruction, use is made of the absorption distribution resulting from a complete reconstruction of layers neighboring one another in the direction of the axis of rotation.

* * * * *